(12) United States Patent
Bousquet

(10) Patent No.: US 6,605,063 B2
(45) Date of Patent: Aug. 12, 2003

(54) TRANSCUTANEOUS ACCESS DEVICE

(76) Inventor: Gerald G. Bousquet, 29 Village Sq., P.O. Box 201, Chelmsford, MA (US) 01824

( * ) Notice: Subject to any disclaimer, the term of this patent is extended or adjusted under 35 U.S.C. 154(b) by 0 days.

(21) Appl. No.: 09/949,122

(22) Filed: Sep. 7, 2001

(65) Prior Publication Data

US 2002/0019610 A1 Feb. 14, 2002

Related U.S. Application Data

(63) Continuation-in-part of application No. 09/430,815, filed on Oct. 29, 1999, now Pat. No. 6,355,020, which is a continuation-in-part of application No. 09/157,977, filed on Sep. 21, 1998, now Pat. No. 6,099,508.

(51) Int. Cl.$^7$ ................................................. A61M 5/32
(52) U.S. Cl. ................................. 604/175; 128/DIG. 26
(58) Field of Search ............................. 604/174, 175, 604/93.01, 104, 264, 164.04, 523, 533, 539, 117; 606/213; 128/DIG. 26

(56) References Cited

U.S. PATENT DOCUMENTS

| | | | | | |
|---|---|---|---|---|---|
| 4,787,882 A | * | 11/1988 | Claren | ...................... | 604/6.16 |
| 4,886,502 A | * | 12/1989 | Poirier et al. | ................ | 604/175 |
| 5,171,216 A | * | 12/1992 | Dasse et al. | ................... | 604/43 |
| 5,807,341 A | * | 9/1998 | Heim | ......................... | 604/174 |
| 5,810,885 A | * | 9/1998 | Zinger | ......................... | 606/213 |
| 5,897,531 A | * | 4/1999 | Amirana | ..................... | 604/180 |
| 6,042,569 A | * | 3/2000 | Finch et al. | ................ | 604/175 |
| 6,440,120 B1 | * | 8/2002 | Maahs | ........................ | 604/523 |

* cited by examiner

Primary Examiner—Brian L. Casler
Assistant Examiner—Cris L. Rodriguez
(74) Attorney, Agent, or Firm—Cesari and McKenna, LLP

(57) ABSTRACT

A transcutaneous access device comprises a sleeve having a flexible extensible main body with opposite ends defining collars. A catheter is loosely received in the main body and extends through the collar. Connecting means permanently connect each collar to the catheter and an annular flexible skirt snugly surrounds the main body. In some device embodiments, the skirt is adjustable along the sleeve and/or the sleeve is bifurcated to accommodate two catheters for optimum fluid flow.

7 Claims, 4 Drawing Sheets

TRANSCUTANEOUS ACCESS DEVICE

RELATED APPLICATIONS

This application is a continuation-in-part of Ser. No. 09/430,815, filed Oct. 29, 1999, now U.S. Pat. No. 6,355,020, which is a continuation-in-part of Ser. No. 09/157,977, filed Sep. 21, 1998 now U.S. Pat. No. 6,099,508.

FIELD OF THE INVENTION

This invention relates to a transcutaneous access device. It relates more particularly to a device of this type to facilitate access to the body through the skin by catheters and similar percutaneous devices.

BACKGROUND OF THE INVENTION

There has of late been increasing use of catheters to provide prolonged or repeated access to the internal organs of chronically ill patients. For example, catheters are used to access a patient's venous system for the administration of intravenous (IV) fluids, antibiotics, and chemotherapy. Catheters are also implanted in patients who require repeated access to the peritoneum for peritoneal dialysis.

Other than occlusion, the most common complications arising with long-standing implants are exit-site infection, tunnel infection, local abscesses and even sepsis. Many of these complications arise because the skin adjacent to the catheter does not heal to form a tight barrier to infection. Rather, epidermal cells tend to invaginate or migrate inward along the catheter and never form a tight biological seal around the catheter. Also, tunnels are created through which body fluids may exude thereby creating a site for infection.

In an attempt to overcome these problems, a catheter has been devised which includes a button-like skirt with a raised neck and a central hole for accommodating a tube. The tube has a corrugated segment extending above the button neck which allows the external portion of the tube to be flexed so as to absorb shocks. The skirt, including a portion of the neck thereof, is covered with a porous material, such as polyester velour, to allow for cell infiltration. When that device is implanted, the epidermal cells tend to migrate or invaginate downward along the neck to the skirt where they form a biological seal with the collagen and subcutaneous tissue growth on the porous covering of the button; see U.S. Pat. No. 4,886,502.

While that concept was relatively successful in animals, it has had limited success in human trials because normal body motions caused stretching of the tissue adjacent to the catheter and exerted torsion on the catheter. Such movements of the tissue relative to the button, which is held stationary by the external segment of the catheter tube, results in disruption of the biological seal between the catheter and the adjacent tissue. Such disruption may also occur when the external segment of the catheter tube is moved accidentally or intentionally when connecting and disconnecting the catheter tube to the infusate source.

SUMMARY OF THE INVENTION

Accordingly, the present invention aims to provide a transcutaneous access device for a catheter which should circumvent most of the problems caused by relative movement of the catheter and the tissue surrounding the catheter.

Another object of the invention is to provide a transcutaneous access device which, when implanted, provides a tight biological seal between the device and adjacent tissue.

A further object of the invention is to provide a device of this type which reduces the risk of infection.

A further object is to provide such a device which allows a high fluid flow rate through the device.

Yet another object of the invention is to provide a transcutaneous access device which is relatively easy to manufacture in quantity.

Other objects will, in part, be obvious and will, in part, appear hereinafter. The invention accordingly comprises the features of construction, combination of elements and arrangement of parts which will be exemplified in the following detailed description, and the scope of the invention will be indicated in the claims.

The transcutaneous access device of this invention comprises a flat button with an opening therethrough and an integral upstanding tubular neck in registration with that opening. Formed as an integral extension of that neck is a flexible, extensible sleeve e.g. elastic tubing or a bellows, whose free end is terminated by a collar which connects to a conventional access catheter whose catheter tube extends all the way through the lumen formed by the sleeve or tube, neck and button of the access device.

In accordance with the invention, the lumen of the present device is large enough to provide appreciable clearance between the walls of the lumen and the access catheter so as to minimize contact between the access device and the access catheter. Thus, when the device is implanted, the collar and upper end segment of the catheter tube are free to move relative to the button and surrounding tissue.

In one preferred embodiment of the invention, the access device is permanently connected, via the free end of the sleeve, to the catheter. In another embodiment, two similar access devices are positioned back to back on the catheter with the free ends of their sleeves connected to the catheter, preferably such that the sleeves are in a collapsed condition. Another embodiment provides a high fluid flow rate through the device.

BRIEF DESCRIPTION OF THE DRAWINGS

For a fuller understanding of the nature and objects of the invention, reference should be had to the following detailed description taken in connection with the accompanying drawings, in which.

DESCRIPTION OF THE PREFERRED EMBODIMENT

Figure 1:
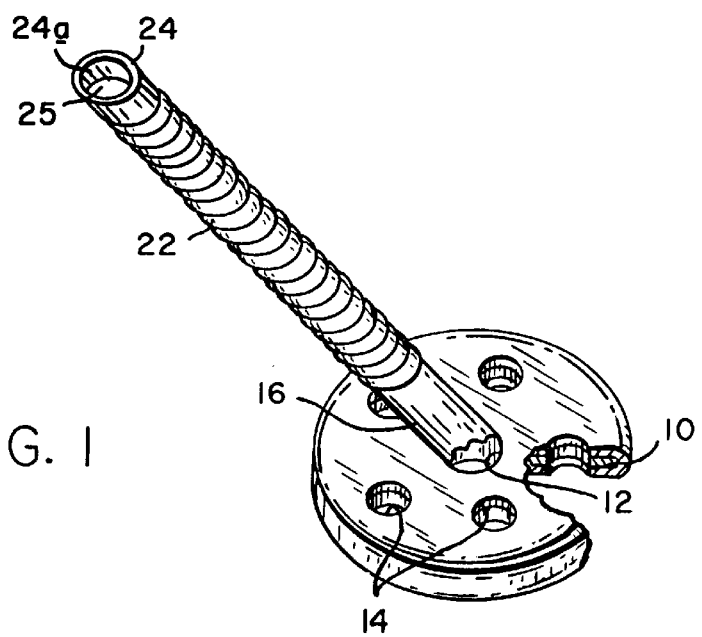
FIG. 1 is an isometric view with parts broken away of a transcutaneous access device incorporating the invention.
Figure 2:
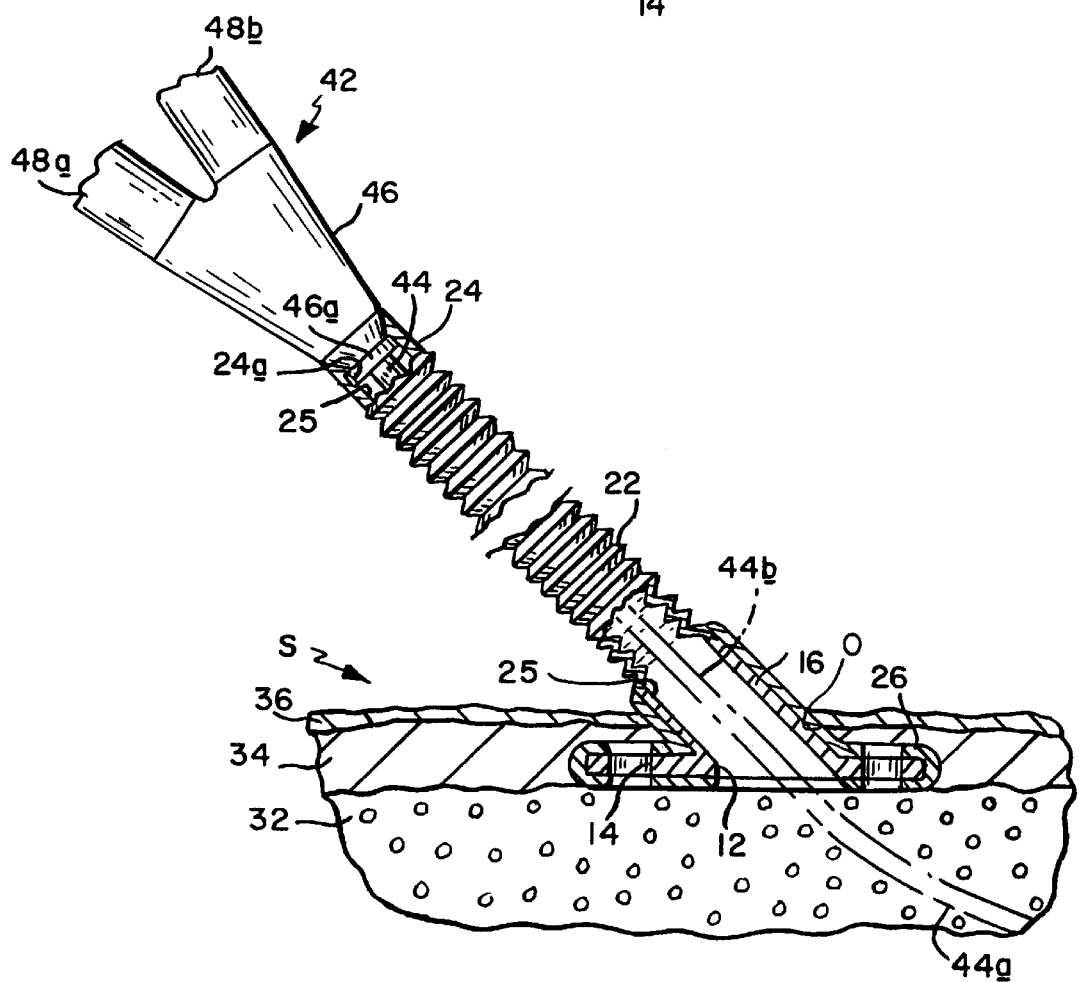
FIG. 2 is a sectional view with parts in elevation showing the FIG. 1 access device implanted in the body and ready for use.

Referring to FIGS. 1 and 2 of the drawing, one embodiment of my access device comprises a flat, button-like main body or skirt 10 having a central opening 12 and an array of three to six through-holes 14 distributed around opening 12. Extending out from one side of skirt 10 in registration with opening 12 is an integral, tubular neck 16 whose lumen is in registration with opening 12. Skirt 10 and neck 16 should be stiff enough to maintain their shapes but be somewhat flexible and compliant so that when implanted they flex and "give" with the patient's dermis. In the illustrated device, the neck 16 extends out from skirt 10 at an angle; however, the neck could just as well be perpendicular to the skirt 10.

The device also includes a highly flexible, extensible tubular sleeve 22 extending from the free end of neck 16. In the FIGS. 1 and 2 device, sleeve 22 is a pleated accordion-like tube which forms a bellows and which is terminated at its free end by a cylindrical collar 24. Thus, the sleeve 22 allows the collar 24 to be moved toward and away from neck 16 in the order of 2–5 cm, as well as in all directions about the longitudinal axis of neck 16. The skirt 10, neck 16, sleeve 22 and collar 24 define a continuous, uniformly sized lumen 25 which extends through the entire device.

As best seen in FIG. 2, the collar 24 is formed with an internal lip 24a to provide a mechanical connection to an associated access catheter as will be described later.

The access device, including the skirt 10, neck 16, sleeve 22 and collar 24 are preferably formed of a flexible, thermally stable, biocompatible material such as flexible, medical grade polyurethane. The accordion-like sleeve 22 may be configured by placing a tubular extension of the neck 16 in a heated female mold and applying gas pressure inside the tube to force the tube walls to conform to the mold. The neck may then be secured to the button-like skirt 10 by welding. Alternatively, the device may be molded as a unitary part.

Preferably, the entire surface of the body or skirt 10 is covered by a porous covering or bed 26 of a material such as medical grade polyester (Dacron) velour. Such a covered skirt 10 is available as Part No. 600K61121, from the U.S. Catheter and Instrument Company of Glenfalls, N.Y. The covering encourages cell infiltration and the formation of subcutaneous tissue and collagen and thus obtains a better bond than the PTFE material used in the above patent.

Typically, when the access device is used for peritoneal dialysis, the skirt 10 is in the order of 2.5 cm in diameter, the neck 16 is about 0.5 cm long, the sleeve 22 is about 2 to 24 cm long and the diameter of the device's lumen 25 is in the order of 0.4 to 0.8 cm. On the other hand, when the device is used for vascular access, skirt 10 may be smaller, e.g., 1 cm in diameter, with the lengths of the neck and sleeve being 0.5 cm and 4 cm, respectively. In that event, the lumen 25 diameter may be in the order of 0.3 to 0.5 cm.

Referring to FIG. 2, the access device is implanted so that the skirt 10 is anchored in the subcutaneous tissue 32 and the covered neck 16 extends out through the dermal layer 34 and epidermal layer 36 of the skin S through an opening O. In time, tissue growth penetrates the through-holes 14 to help anchor the access device. Those same holes also allow for fluid drainage and for tissue ingrowth. As noted previously, the covering 26 provides a porous bed to encourage the growth of tissue and collagen around the body 10 to provide a biological seal with the epidermal cells which migrate or invaginate down around neck 16 until they reach the covering 26.

The access device also includes an access catheter or catheter tube such as the one shown generally at 42 in FIG. 2. The illustrated catheter is a vascular access catheter. However, the catheter could just as well be a peritoneal access catheter. Suffice it to say that the catheter 42 includes a tube 44 which has an internal segment 44a which extends from the skin line along neck 16 and through body 10 to a selected infusion site such as the subclavian vein. The catheter tube also includes an external segment 44b which extends from the skin line through sleeve 22 and collar 24 to a Y-fitting 46 to which is connected a pair of fluid inlet tubes 48a and 48b so as to allow fluid from two different sources to be flowed to the catheter tube 44.

When the catheter 42 is properly seated in the access device, the lip 24a of the device's collar 24 is arranged to releasably engage over a radial flange 46a usually present at the lower end of the catheter fitting 46 to mechanically connect the catheter to the access device at the free end of the device's flexible sleeve 22. However, as noted previously, the device's lumen 25 is sized to minimize contact with the catheter tube 44 and so as not to inhibit motion of the catheter tube. Therefore, any motion of the internal catheter tube segment 44a caused by movements of the patient's body is substantially decoupled from the implanted portions of the access device, i.e., skirt 10 and neck 16. By the same token, if the external segment 44b of the catheter tube 44 should be moved accidentally or intentionally when connecting or disconnecting the catheter, the accordion-like sleeve 22 is able to flex, extend and contract as needed to accommodate such movement so that essentially no motion is coupled to the implanted portions of the access device. Resultantly, a tight biological seal is maintained between the access device and the surrounding tissue.

Indeed, actual experiments with prototype devices have shown that there are no signs of infection at the implantation sites even after the devices have been in place for prolonged periods.

Figure 3:
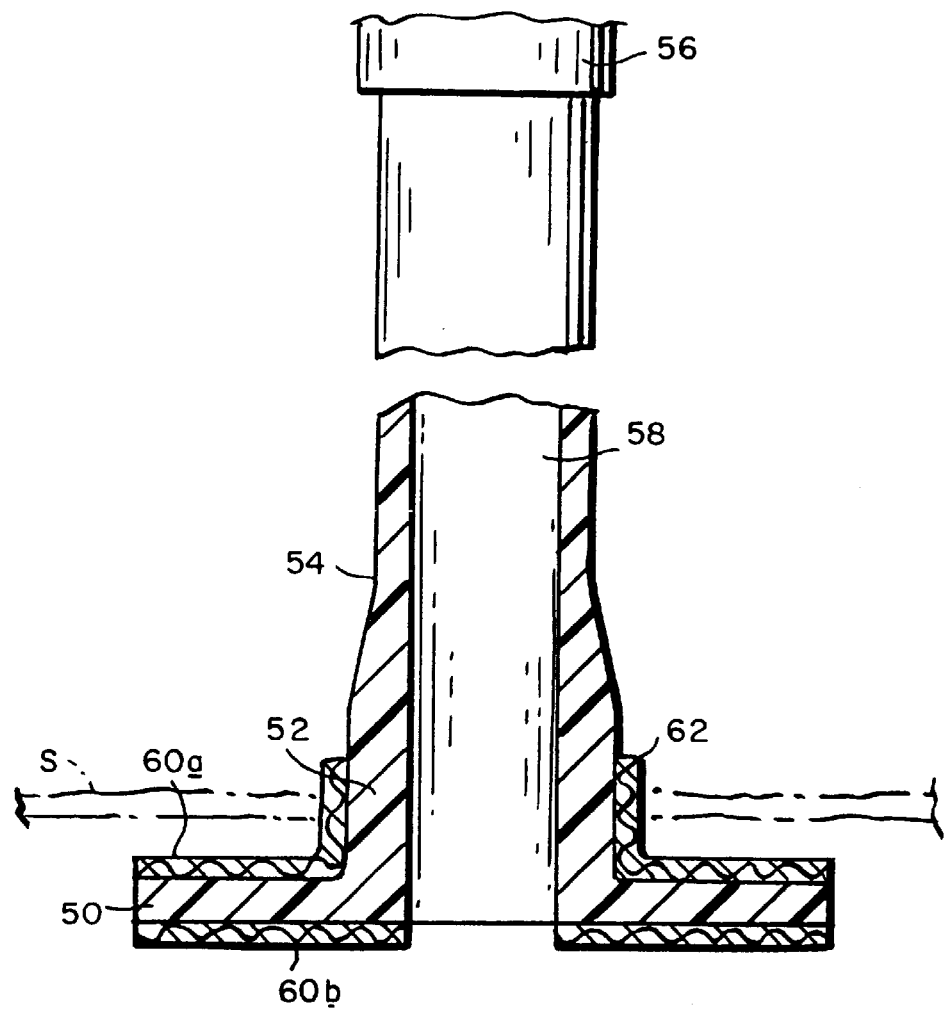
FIG. 3 is a view similar to FIG. 1 of another embodiment of the access device.

Refer now to FIG. 3 which shows a second embodiment of my transcutaneous access device. It is similar to the FIG. 1 embodiment, except that its button-like skirt 50, tubular neck 52 and extensible sleeve 54 are formed as a unitary part. An annular connector member 56 which may be similar to member 24 is provided at the free end of the sleeve 54. Thus, the device has an axial passage or lumen 58 which extends the entire length of the device for accommodating a catheter tube 44 shown in phantom in FIG. 3. A suitable material for the button-neck-sleeve unit is medical grade polyurethane sold under the designation Tecoflex EG 80A by Thermedics, Inc., Woburn, Mass.

In this case, the extensible sleeve 52 is not accordion-like. Rather, it is a thin-walled (e.g., 0.030 in.), elastic tube which can readily flex and extend lengthwise by the required amount, i.e., a few centimeters.

For most applications, sleeve 52 is more flexible and extensible than skirt 50 and neck 52. To achieve this result, the device is formed so that the skirt and neck have a greater wall thickness than the sleeve.

As in the FIG. 1 device, porous bed material is applied to exterior surfaces of the skirt 50 and neck 52. This material may be the same as or similar to the material used for bed 26 described above. Here, however, the material is applied in two parts. An annular piece 60a of bed material is slid onto the sleeve 54 and neck 52 and folded as shown in FIG. 3 so that it covers the upper surface of the skirt and encircles the neck 52. It may be secured there by any suitable adhesive. To assure placement of the material piece 60a at the correct elevation on the neck 52 indicium 62 may be molded into or inscribed around neck 52.

Another annular piece 60b of bed material is adhered to the undersurface of skirt 50, the opening through piece 60b being substantially the same size as lumen 58.

After being secured to skirt 50, the bed material pieces 60a and 60b may be trimmed so that their outer edges are even with the periphery of skirt 50.

The FIG. 3 embodiment of the device has all of the attributes of the FIG. 1 embodiment and functions in the same way described above in connection with the FIG. 1 embodiment.

Figure 4:
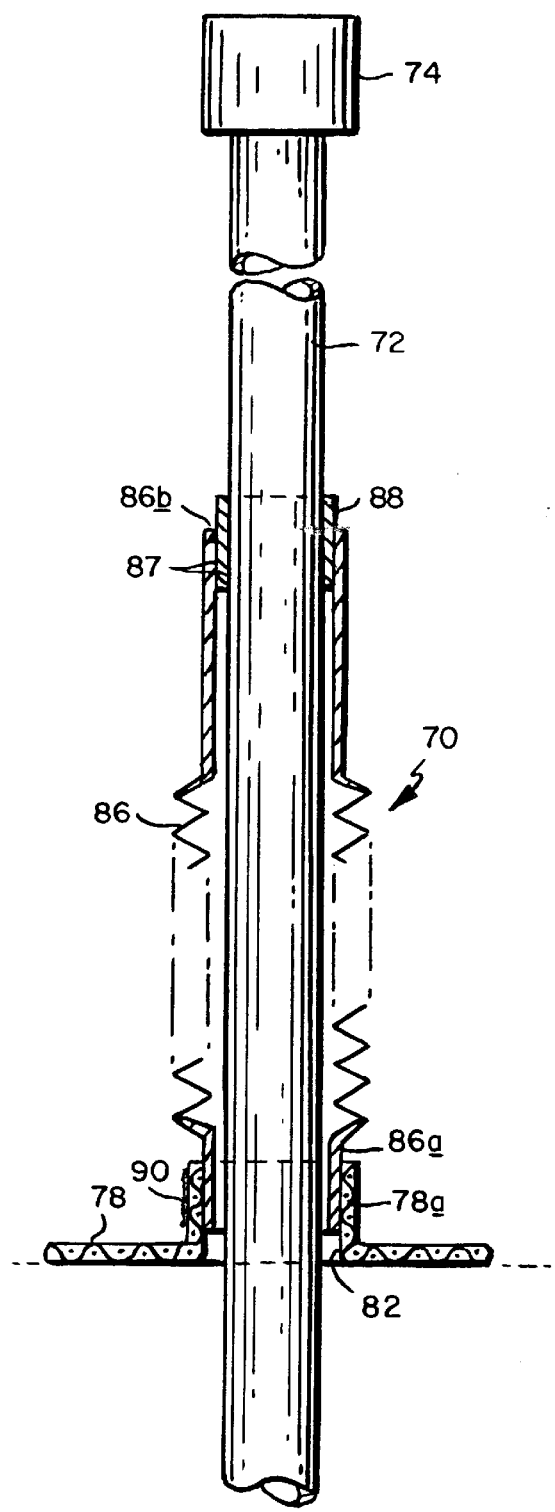
FIG. 4 is a sectional view with parts in elevation showing yet another embodiment of the invention.

In many applications it is desirable to minimize the length of the annular space between the access device and the catheter tube extending through that device. FIG. 4 illustrates an access device 70 which accomplishes this objective. The device includes a catheter tube 72 having a standard connector 74, e.g., a Luer, at its outer end.

This access device 70 includes an annular flexible skirt 78 having a central opening 82 and an upstanding neck 78a both of which are appreciably larger than the outer diameter of tube 72. Neck 78a is permanently bonded to a flange 86a formed at the lower end of a flexible, extensible sleeve or extension 86, e.g., a bellows (FIG. 4) or elastic tube (FIG. 3), having a collar 86b at its opposite or upper end. As with the other device embodiments, means are provided for connecting the collar 86b to the catheter tube. In this case, however, the connecting means are constituted by a bonding 87 of collar 86b to the tube. If desired, an adapter sleeve 88 may be present between tube 72 and collar 86b to improve the bond. The sleeve 86, including its flange 86a and collar 86b, has an inside diameter that is appreciably larger than that of tube 72 so that the neck 78a, skirt opening 82, sleeve 86, flange 86a and collar 86b define a continuous lumen which extends through the entire device 70. This allows the collar 86b to be moved toward and away from skirt 78 as well as in all directions about the longitudinal axis of the skirt.

As with the other access device embodiments, preferably skirt 78 is made of or covered by a porous material, e.g. polyester, velour, which encourages cell ingrowth. Also, holes may be provided in the skirt.

As is apparent from FIG. 4, only a single tube extends from collar 86b to connector 74. Therefore, there is no annular space around that segment of the tubing which could be a site for unwanted bacterial growth.

Figure 5:
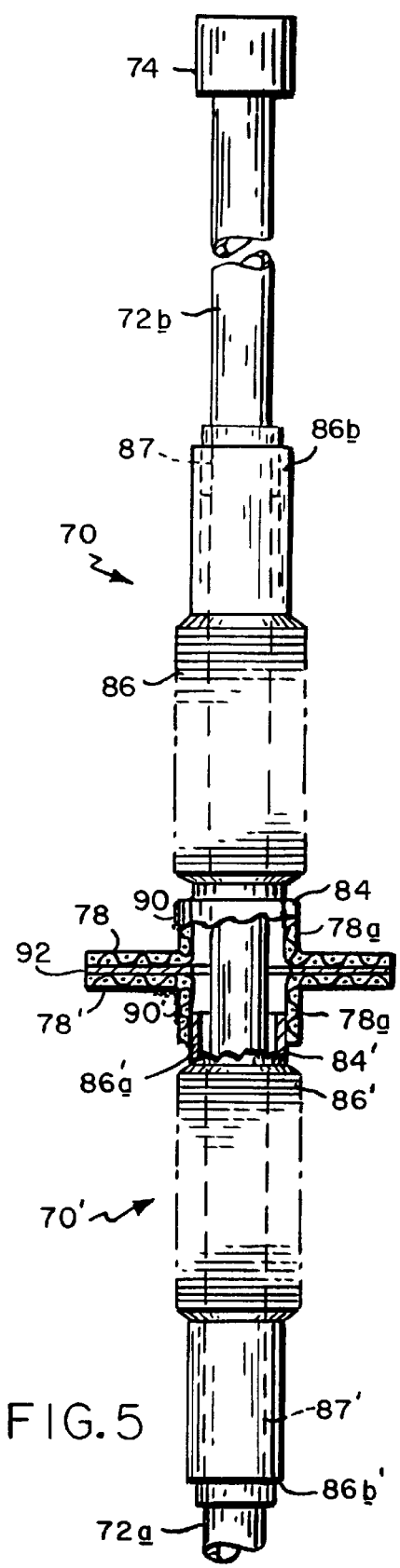
FIG. 5 is a view in elevation of a further invention embodiment.

Refer now to FIG. 5 which illustrates yet another embodiment of my invention consisting essentially of two of the access devices depicted in FIG. 4 positioned back to back on catheter tube 72. The two mirror-image access devices are shown generally at 70 and 70' and their corresponding parts carry the same identifying numerals (primed and unprimed) as in FIG. 4. The skirts 78 and 78' of the two access devices are connected together by adhesive bond 92 or the like and the collars 86b, and 86b' of the two devices are bonded or otherwise secured to tubing 72. Thus, the two skirts 78, 78' are free to float relative to the catheter tube 72 and the collars.

Preferably, the collars 86b, 86b' are connected to tube 72 such that the two sleeves 86, 86' are under some compression, e.g., the bellows (FIG. 4) are collapsed to some extent. This assures that when the access device is implanted so that the skirts 78, 78' are anchored in subcutaneous tissue, any tension on the internal catheter tube segment 72a caused by movements of the patient's body is substantially decoupled from the implanted portions of the device, i.e., the skirts 78, 78' and necks 78a, 78a'. Likewise, if the external segment 72b of the catheter tube 72 should be moved accidentally or intentionally when connecting or disconnecting the catheter, the external sleeve 86 is able to flex, extend and contract as needed to accommodate such movement. Resultantly, no motion is coupled to the implanted portions of the access device which could upset the biological seal maintained between skirts 78, 78' and the surrounding tissue.

Of course, in the FIG. 5 device, the two skirt layers 78, 78' could be combined into a single skirt with necks projecting from opposite faces of that skirt.

Figures 6, 7:
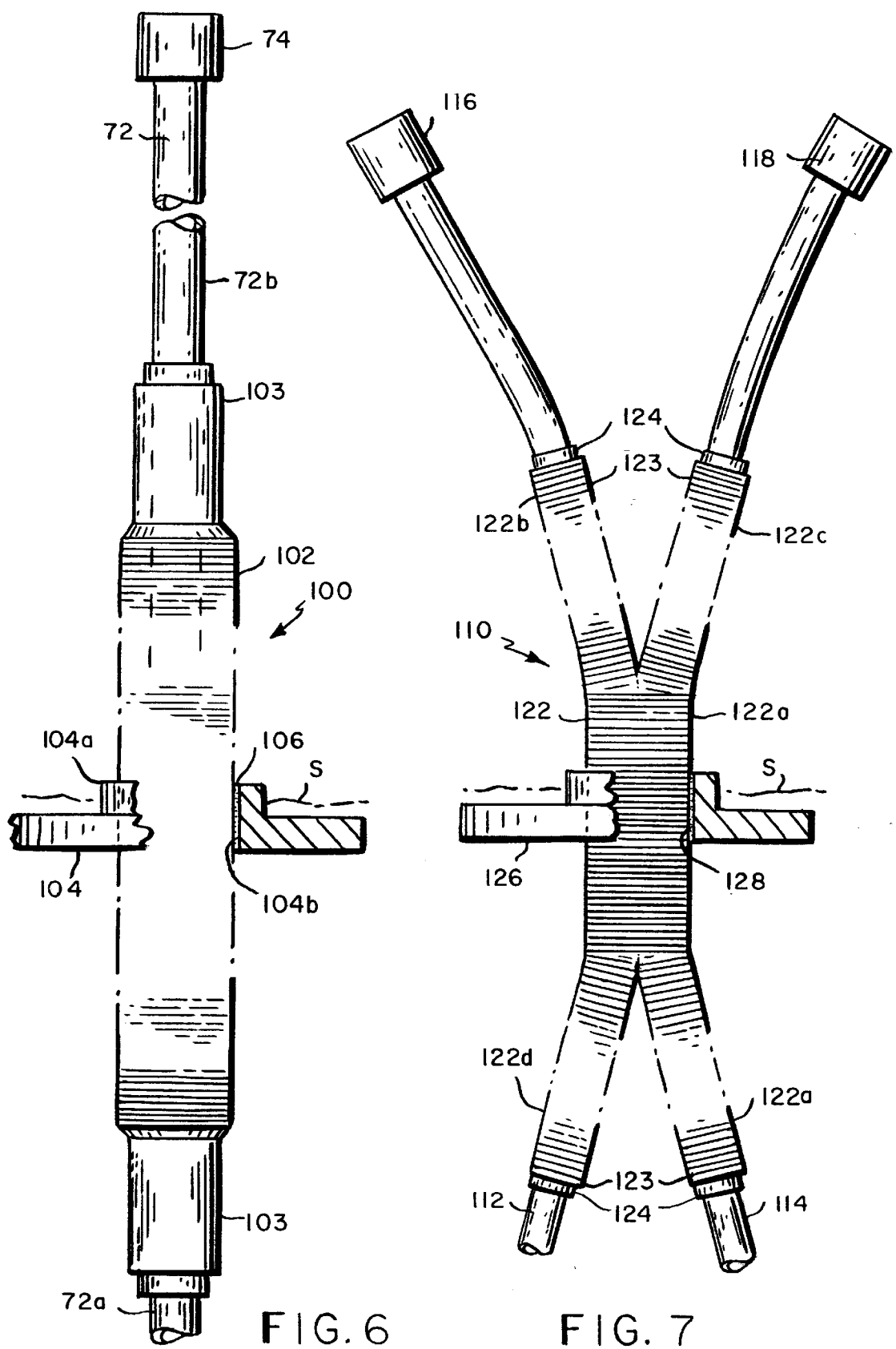
FIG. 6 is a similar view of still another device embodiment.
FIG. 7 is a similar view of a high flow rate access device incorporating the invention.

In the back-to-back type access device depicted in FIG. 5, a par of bellows or elastic tubes 70, 70' are permanently bonded to the internal and external tube segment 72a and 72b, respectively. In some applications, it may be desirable to employ a single bellow or elastic tube. FIG. 6 shows generally at 100 an access device of this type. It comprises a single flexible, extensible sleeve 102 in the form of a bellows or elastic tube which loosely receives a single length of tubing 72 as in the FIG. 5 device. The opposite ends of the sleeve define collars 103 which are permanently bonded to tube 72 preferably such that sleeve 102 is under some compression. The access device 100 has a skirt 104 and neck 104a with a central opening 104b which snugly receives the sleeve. A bonding 106 permanently secures the skirt 104 to sleeve 102 midway along the sleeve.

Thus when the access device 100 is implanted, the distal end of the tube segment 72a may be positioned at the infusion site and the skirt 104 positioned so that the skirt can be placed in the tissue under the patient's skin line S, the skirt moving relative to tube 72 subcutaneously as necessary.

Refer now to FIG. 7 which shows generally at 110 another embodiment of my access device which allows for a relatively high rate of fluid flow through the device. More particularly, in some cases it may be desirable to effect cathetertization using a catheter with dual side-to-side lumens. For example, for central venous access, it is desirable to go to the right internal jugular vein because it offers a direct route to the vena cava and atrium junction. For patient compliance, the vein puncture is sought immediately above or behind the clavicle and the catheter(s) have an anterior exit in parallel with the sternum. When dual catheters are employed to maximize fluid flow, the catheters usually exit the patient at different places at the patient's skin line S. This means that there are two different sites for infection to occur. FIG. 7 depicts an embodiment of my transcutaneous access device which can accommodate two different catheters for increased fluid flow, yet which has all of the advantages described above for the other device embodiments, particularly the one shown in FIG. 6.

The access device 110 comprises a pair of catheter tubes 112 and 114 which may be identical. The upper or outer end of tube 112 is provided with a connector 116. A similar connector 118 is provided at the upper end of catheter tube 114. Both of these tubes may be the same as or similar to the catheter tube 72 described above.

Surrounding comparable lengthwise segments of tubes 112 and 114 is a flexible resilient sleeve 122, e.g. a bellows or elastic tube, which is bifurcated at its upper and lower ends. In other words, the sleeve 122 has a main axial segment or body 122a whose diameter is large enough to loosely surround both catheter tubes 112 and 114. At the upper end of the main segment 122a, sleeve 122 divides to form two smaller diameter branches 122b and 122c, the former branch accommodating or receiving tube 112 and the latter branch receiving tube 114. Similar branches 122d and 122e extend from the lower end of main segment 122a to separately accommodate tubes 112 and 114. Thus, tube 112 may extend through branch 122b main segment 122a and branch 122d while tube 114 may extend through branch 122c, main segment 122a and branch 122e. The free ends of all of the branches define collars 123 which are permanently secured to the corresponding tubes 112, 114 by bondings 124 or other suitable means.

Surrounding the main segment 122a of sleeve 122 is an annular flexible skirt 126 which may be of a similar construction as the skirts of the other device embodiments described above. Skirt 126 may be permanently secured at a fixed location along the main segment 122a. by a bond 128.

Preferably also, the collars 123 are connected to the respective tubes 112 and 114 such that the sleeve 122 is under some compression, e.g. the bellows are collapsed to some extent. Resultantly, when the access device is implanted so that its skirt 126 is anchored in subcutaneous tissue, tension on the implanted catheter tube segments caused by movements of the patient's body are substantially decoupled from the fixed portion of the device, i.e. skirt 126.

The access device depicted in FIG. 7 has a sleeve 122 in the form of a bellows whose branches are also flexible and extensible, i.e. smaller bellows. For those applications wherein the sleeve 122 only has to provide a relatively small amount of flexibility and/or extension, it may suffice that only the main segment 122a be extensible. In other words, in that event, the branches 122b to 122e may be smaller diameter sleeves whose free ends form the collars 123 secured to the corresponding catheter tubes 112 and 114. Thus, the forming of the entire sleeve 122 as a bellows maximizes the amount of relative movement that can occur between the ends of tubes 112, 114 and the skirt 126.

As seen from the foregoing, my transcutaneous access device is, for the most part, composed of plastic parts which can be made in quantity relatively easily and inexpensively. Therefore, it should find wide application wherever it is necessary to maintain catheters in situ for a long period of time.

It will thus be seen that the objects set forth above, among those made apparent from the preceding description, are efficiently attained and, since certain changes may be made in the above construction without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention described herein.

What is claimed is:

1. A transcutaneous access device comprising
    a sleeve having a flexible extensible main body with opposite ends defining collars;
    a catheter having a first end and being loosely received in said main body and extending through said collars;
    connecting means permanently connecting said collars to the catheter;
    an annular flexible skirt having an inner edge snugly surrounding the sleeve, and
    means for securing the skirt to the sleeve at a location between the ends of said sleeve.

2. The device defined in claim 1 wherein the entire inner edge of the skirt is bonded to the sleeve.

3. The device defined in claim 1 wherein said sleeve comprise a bellows.

4. The device defined in claim 1 wherein said sleeve comprises a thin-walled elastic tube.

5. The device defined in claim 1 wherein said sleeve is under compression.

6. The device defined in claim 1 and further including a connector connected to the first end of the catheter.

7. The device defined in claim 1
    wherein the sleeve is bifurcated at both ends to form first and second pairs of branches and said catheter extends through one branch of each pair of branches, and
    further including a second catheter extending through the other branch of each pair of branches.

* * * * *